United States Patent [19]

Inamoto et al.

[11] 4,059,643

[45] Nov. 22, 1977

[54] PROCESS FOR HYDRIDE TRANSFER REDUCTION REARRANGEMENT OF 8-EXO-HYDROXYMETHYL-ENDO-TRICYCLO 5.2.1.0$^{2,6}$] DECANE TO FORM TRICYCLO[5.3.1.0$^{3,8}$] UNDECANE

[75] Inventors: Yoshiaki Inamoto; Yoshiaki Fujikura, both of Wakayama; Kiyoshi Tsuchihashi, Kainan; Eiji Kashihara, Wakayama, all of Japan

[73] Assignee: Kao Soap Co., Ltd., Tokyo, Japan

[21] Appl. No.: 744,957

[22] Filed: Nov. 26, 1976

[30] Foreign Application Priority Data

Dec. 4, 1975    Japan ............................. 50-144673

[51] Int. Cl.$^2$ ............................................. C07C 13/54
[52] U.S. Cl. ........................ 260/666 PY; 260/666 M; 260/617 R
[58] Field of Search ......... 260/666 M, 666 PY, 617 R

[56] References Cited

U.S. PATENT DOCUMENTS

3,976,710    8/1976    Takaishi et al. ................ 260/666 M

OTHER PUBLICATIONS

Naotake Takaishi et al., J. Org. Chem., vol. 41, No. 5, 771–775, 1976.
Naotake Takaishi et al., J. Org. Chem., vol. 40, No. 3, 276–281, 1975.
Naotake Takaishi et al., J. Org. Chem., vol. 40, No. 10, 1483–1487, 1975.

*Primary Examiner*—Veronica O'Keefe
*Attorney, Agent, or Firm*—Blanchard, Flynn, Thiel, Boutell & Tanis

[57] ABSTRACT

The hydride transfer reduction rearrangement of 8-exo-hydroxymethyl-endo-tricyclo [5.2.1.0$^{2,6}$] decane in the presence of concentrated sulfuric acid and a hydride source provides 4-homoisotwistane (tricyclo [5.3.1.0$^{3,8}$] undecane).

6 Claims, No Drawings

PROCESS FOR HYDRIDE TRANSFER REDUCTION REARRANGEMENT OF 8-EXO-HYDROXYMETHYL-ENDO-TRICYCLO 5.2.1.0$^{2,6}$] DECANE TO FORM TRICYCLO[5.3.1.0$^{3,8}$] UNDECANE

FIELD OF THE INVENTION

The present invention relates to a process for hydride transfer reduction rearrangement of 8-exo-hydroxymethyl-endotricyclo [5.2.1.0$^{2,6}$] decane, More particularly, the present invention relates to a process for isomerizing 8-exo-hydroxymethyl-endo-tricyclo- [5.2.1.0$^{2,6}$] decane of formula (I):

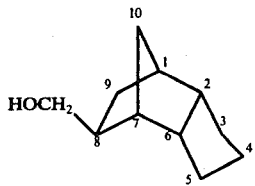
(I)

in the presence ofoncentrated sulfuric acid and a hydride source and simultaneously reducing the same with a hydride to synthesize 4-homoisotwistane (tricyclo [5.3.1.0$^{3,8}$] undecane) of formula (II):

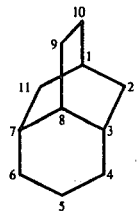
(II)

SUMMARY OF THE INVENTION

4-Homoisotwistane of formula (II) is a compound found recently by Krantz [Chem, Commun., 1287 (1971); J. Amer. Chem. Soc., 95, 5662 (1973)], which is a new tricycloundecane having the same skeleton as that of seychellene, i.e. one of the sesquiterpenes. After investigations on various functional reactions of compound (II), the inventors found previously that 3-amino-4-homoisotwistane, i.e. one of the resulting derivatives, is a very effective antiviral drug (Japanese Patent Application No. 93968/1975). Thus, the final product of formula (II) of the present invention is a very useful substance as a starting material for preparing drugs for both human beings and animals.

In an embodiment, the present invention can be carried out very simply by stirring the starting alcohol of formula (I) with concentrated sulfuric acid and a hydrocarbon which is a hydride source at room temperature. After completion of the reaction, the hydrocarbon layer is taken out, from which the hydrocarbon is removed by a suitable means such as distillation to obtain the crude product in a yield of 30-40%. Selectivity to the desired product of formula (II) is as high as 93%. Generally in the acid catalyzed isomerization reaction of tricycloundecanes, if the isomerization reaction is stopped in the course of the reaction, not completing the reaction for obtaining the desired methyladamantane, the product rarely comprises a sole compound, but rather a complex mixture of numerous tricycloundecane isomers is obtained [the inventors J. Org. Chem., 40, 276 (1975); and 1483 (1975)]. It is surprising, therefore, that the compound of formula (II) is obtained at a selectivity of as high as 93% according to the process of the present invention. This fact indicates the usefulness of the process of the present invention for synthesizing the compound of formula (II).

The concentrated sulfuric acid employed in the process of the invention has a concentration of 75-100%, preferably 90-98%. If the concentration of sulfuric acid is less than 75%, effective isomerization is impossible and, on the other hand, if the concentration of sulfuric acid is higher than 100% (fuming sulfuric acid), an oxidation reaction is also caused to reduce the yield of the desired product. Sulfuric acid is used in an amount ranging from the equivalent to 1000 times the weight of starting alcohol of formula (I), preferably 10-100 times the weight of the latter.

As the hydride source, any aliphatic and alicyclic hydrocarbons having a carbon atom number 5 to 10 is useful. However, the use of hydrocarbons having too high boiling points should be avoided, since separation of them from the desired product (II) is difficult. As the hydride sources, there may be mentioned, for example, n-pentane, n-hexane, n-heptane, n-octane, cyclopentane, cyclohexane, cyclooctane, methylcyclohexane and isooctane, and the mixture thereof, petroleum ether.

Although the amount of the hydride source does not exert a great influence on the yield of the desired product of formula (II), it is used preferably in an amount in the range of 1-1000 more as the preferably 10-100 times as much weight of starting alcohol of formula (I). Reaction temperature may be in the range of from −20° C to 100° C, pref. 0° to 80° C, a temperature around room temperature (20° -30° C) being optimum.

The starting material of the present invention, i.e. 8-exo-hydroxymethyl-endo-tricyclo [5.2.1.0$^{2,6}$] decane can be synthesized, for example, by hydrogenation of 8- and 9-exo-formyl-endo-tricyclo [5.2.1.0$^{2,6}$] deca-3-ene synthesized by oxo reaction of endo-tricylo [5.2.1.0$^{2,6}$] deca-3,8-diene in the presence of a rhodium catalyst.

The following example further illustrates the present invention:

EXAMPLE

A mixture comprising 1.0 g of 8-exo-hydroxymethyl-endo-tricyclo [5.2.1.0$^{2,6}$] decane, 10 g of 95% sulfuric acid and 50 ml. of n-pentane is stirred vigorously at room temperature for 10 minutes. The reaction mixture is allowed to stand and the resulting n-pentane layer is taken out, washed with water and dried with calcium chloride. After distillation of n-pentane from the dried mixture, 0.41 g (yield 45%) of crude product is obtained as distillation residue. The product is subjected to analysis according to gas chromatography-mass spectrometry to reveal that 93% of 4-homoisotwistane of formula (II) is contained therein. The crude product is purified by sublimation under reduced pressure to obtain 0.35 g (yield 39%) of pure compound of formula (II). MP, IR, $^1$HNMR and MS of the resulting compound of formula (II) coincided with those of the standard [the inventors' J. Org. Chem., 40, 276 (1975)].

4-homoisotwistane can be converted into 3-bromo-4-homoisotwistane by bromination with liquid bromine. Further, 3-bromo-4-homoisotwistane can be subject to Ritter reaction with concentrated sulfuric acid in acetonitrile to give 3-acetamino-4-homoisotwistane. Still further, 3-acetamino-4-homoisotwistane can be converted into 3-amino-4-homoisotwistane by alkali hydrolysis. An acid salt of 3-amino-4-homoisotwistane has bioactivity.

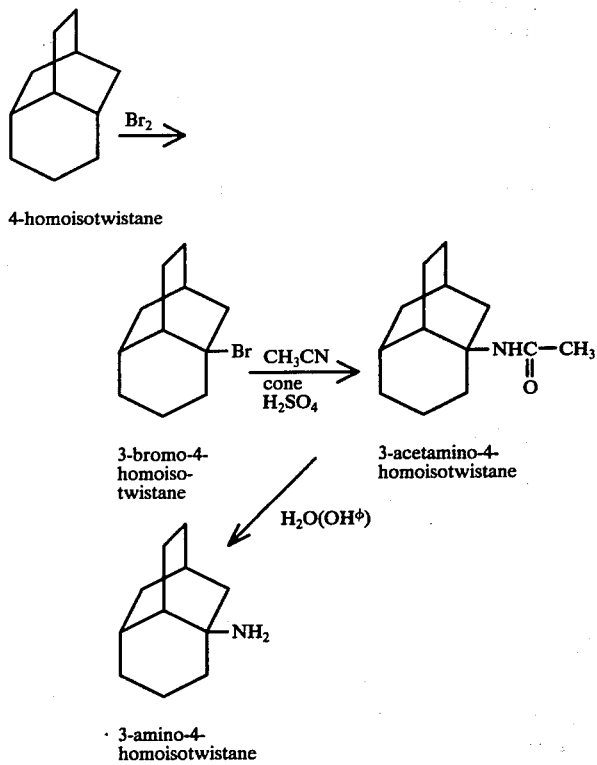

3-Amino-4-homoisotwistane acid salts exhibit apparent inhibition of an viral growth in a 1/10 concentration, as compared to that of adamantylamine hydrochloride which is well known as an antiinfluenza virus agent.

These findings are shown below with the experimental results.

After chick embryo fibroblast cells were cultivated in a test tube for 2 to 3 days, the medium was inoculated with Newcastle disease virus of about 128 HAU (Hemagglutination Unit). To the upper layer was added a culture medium of the stepwise dilution system containing the following compounds, and the resulting mixture was then cultivated at 37° C for 48 hours and the effects were evaluated based on the hemagglutination reaction.

The results obtained are shown in Table 1.

Table 1

| Compounds | Concentration (μg/ml) | % HAU* | CT** |
|---|---|---|---|
| 3-amino-4-homoiso-twistane hydrochloride | 40 | 0.4 | ± |
|  | 20 | 2.7 | — |
|  | 10 | 5.3 | — |
|  | 5 | 18 | — |
|  | 2.5 | 21 | — |
| Adamantylamine hydrochloride (Control) | 500 | <1.0 | + |
|  | 250 | 9 | + |
|  | 125 | 100 | — |
|  | 62 | 100 | — |

*% HAU = $\dfrac{\text{HAU in the media containing the compounds (Dilution multiple inhibiting hemagglutination)}}{\text{HAU in the blank medium}} \times 100$ Table 1-continued

| Compounds | Concentration (μg/ml) | % HAU* | CT** |
|---|---|---|---|

**CT: the degree of damage on chick embryo fibloblast cells exerted by the test compound
(−) no damage
(±) small eruptions were observed on the surface of the cell
(+) monolayer of chick embryo fibloblast cells was separated from the wall of tube.

The preparation of the formula I compound 8-exo-hydroxymethyl-endo-tricyclo[5.2.1.0$^{2,6}$] decane is described in an application of Yoshiaki Inamoto, Yoshiaki Fujikura and Hiroshi Ikeda entitled "8-Exo-Hydroxymethyl-Endo-Tricyclo[5.2.1.0$^{2,6}$]Decane" being filed concurrently herewith, Ser. No. 744,956, filed Nov. 26, 1976, the entire contents of which are incorporated herein by reference.

The embodiments of the invention in which an exclusive property or privilege is claimed are defined as follows:

1. A process for preparing tricyclo[5.3.1.0$^{3,8}$]undecane having the formula (II), (II)

which comprises, reacting one part by weight of 8-exo-hydroxymethyl-endo-tricyclo[5.2.1.0$^{2,6}$]decane having the formula (I)

(I)

with from 1 to 1000 parts by weight of concentrated sulfuric acid having a concentration of from 75 to 100%, and with from 1 to 1000 parts by weight of a hydrocarbon selected from the group consisting of n-pentane, n-hexane, n-heptane, n-octane, cyclopentane, cyclohexane, cyclooctane, methylcyclohexane, isooctane, petroleum ether and mixtures thereof, at a temperature of from −20° C to 100° C, until a substantial quantity of the formula (II) compound is formed, and recovering the formula (II) compound from the reaction mixture.

2. A process according to claim 1 wherein the concentration of said sulfuric acid is from 90 to 98% and the amount thereof is from 10 to 100 parts by weight per one part by weight of the formula (I) compound.

3. A process according to claim 1 wherein the amount of said hydrocarbon is from 10 to 100 parts by weight per one part by weight of the formula (I) compound.

4. A process according to claim 1 wherein the reaction temperature is from 0° C to 80° C.

5. A process according to claim 1 wherein the hydrocarbon is n-pentane.

6. A process according to claim 4 wherein the reaction temperature is around room temperature.